US009807986B2

(12) United States Patent
Hou et al.

(10) Patent No.: US 9,807,986 B2
(45) Date of Patent: Nov. 7, 2017

(54) METHODS FOR ESTABLISHING ANIMAL MODEL OF HEPATOCELLULAR CARCINOMA BONE METASTASIS

(71) Applicants: Rui Hou, Wuhan (CN); Yuwei Wang, Wuhan (CN); Huifang Liang, Wuhan (CN); Zhanguo Zhang, Wuhan (CN); Zhimin Liu, Wuhan (CN); Binhao Zhang, Wuhan (CN); Bixiang Zhang, Wuhan (CN); Xiaoping Chen, Wuhan (CN)

(72) Inventors: Rui Hou, Wuhan (CN); Yuwei Wang, Wuhan (CN); Huifang Liang, Wuhan (CN); Zhanguo Zhang, Wuhan (CN); Zhimin Liu, Wuhan (CN); Binhao Zhang, Wuhan (CN); Bixiang Zhang, Wuhan (CN); Xiaoping Chen, Wuhan (CN)

( * ) Notice: Subject to any disclaimer, the term of this patent is extended or adjusted under 35 U.S.C. 154(b) by 0 days.

(21) Appl. No.: 15/083,269

(22) Filed: Mar. 28, 2016

(65) Prior Publication Data

US 2017/0273283 A1 Sep. 28, 2017

(51) Int. Cl.

| | |
|---|---|
| ***A01K 67/027*** | (2006.01) |
| ***A61K 49/00*** | (2006.01) |
| ***G01N 33/50*** | (2006.01) |
| ***C12N 5/09*** | (2010.01) |
| ***C12N 9/02*** | (2006.01) |

(52) U.S. Cl.

CPC ........ *A01K 67/0271* (2013.01); *C12N 5/0693* (2013.01); *C12N 9/0069* (2013.01); *C12Y 113/12007* (2013.01); *A01K 2207/12* (2013.01); *A01K 2227/105* (2013.01); *A01K 2267/0331* (2013.01)

(58) Field of Classification Search

None

See application file for complete search history.

(56) References Cited

PUBLICATIONS

Heindryckx (2009) "Experimental mouse models for heptocellular carcinoma research", International Journal of Experimental Pathology, 90(4): 367-86.*

* cited by examiner

*Primary Examiner* — Robert M Kelly

(74) *Attorney, Agent, or Firm* — Matthias Scholl, PC; Matthias Scholl

(57) ABSTRACT

A method for establishing an animal model of hepatocellular carcinoma (HCC) bone metastasis, the method including: 1) establishing 97H and LM3 cell clones with stable expression of firefly luciferase (LUC); 2) allowing HCC cells to form bone metastasis in nude mice via intratibial injection; 3) reproducing HCC bone metastasis in nude mice via intracardiac injection of tumor cells; and 4) isolating a subpopulation of tumor cells that targets metastasis to bone. The 97H and the LM3 are highly metastatic HCC cell lines transfected with luciferase gene. BALB/cA-nu mice are 4-5 weeks old and maintained in laminar flow cabinets under SPF conditions and received human care throughout an entire study. A cell number for intratibial injection is $0.5\times10^6$, and a cell number for intracardiac injection is $1\times10^6$.

3 Claims, 2 Drawing Sheets

METHODS FOR ESTABLISHING ANIMAL MODEL OF HEPATOCELLULAR CARCINOMA BONE METASTASIS

BACKGROUND OF THE INVENTION

Field of the Invention

This invention relates to methods for establishing animal model of hepatocellular carcinoma (HCC) bone metastasis. This invention further relates to HCC liver metastasis and new drug chemical-treatment for HCC bone metastasis which are useful in the treatment and/or prevention of bone metastatic HCC.

Description of the Related Art

Liver cancer is the third most common malignant tumor in the digestive system as well as the third leading cause of cancer mortality in developing countries.

Surgical resection has been widely accepted as the only potentially curative therapy for hepatocellular carcinoma (HCC), the most predominant type of primary liver cancer worldwide. Despite this, the prognosis and 5-year disease-free survival rate remain poor.

The presence of metastases either prevents surgery or contributes to the high rate of recurrence in those patients who have been treated surgically. Due to the improvement of overall survival of HCC patients and the development of various imaging technologies in recent decades, the incidence of bone metastasis in HCC patients significantly increased to reach as high as 28%. Bone metastasis causes severe pain, fractures, and motor dysfunction, and it is largely responsible for much of the morbidity associated with this disease.

Clinical follow-up studies of metastatic patients revealed an extremely poor survival rate (with a median survival time of only 3-7 months) because most patients did not have opportunities to undergo surgical treatment when diagnosed and received only palliative therapy.

Most studies in this area that had been described in the literature are based on retrospective analysis of clinical cases. The lack of a suitable model system had severely impeded research on the biological process and molecular basis of HCC bone metastasis. Bone metastasis frequently occurs in breast cancer, prostate cancer, lung cancer, melanoma, and HCC; corresponding animal models of the former four have been successfully established to promote fundamental research on bone metastasis. The increasingly high incidence and our poor understanding of HCC bone metastasis make the establishment of a suitable model system a priority.

SUMMARY OF THE INVENTION

In view of the above-described problems, it is one objective of the invention to provide a method for establishing a mouse model for HCC bone metastasis. Any improvement in our understanding may offer hope and possible therapeutic agents for the prevention and treatment of this disease.

Intracardiac injection of luciferase-labelled tumor cells has been widely used to establish metastatic models of various types of malignant tumors, including breast cancer, prostate cancer, and renal cell carcinoma.

In our study, metastasis in maxillo-facial region was always detected early in LM3 and 97H inoculated mice. This may be due to the enriched blood supply of this area and its proximity to body surface. Tumor formation and progression in other bones, such as the spine and the hind limbs, could also be detected in the following week, which was further verified via ex vivo BLI and histological analyses. The expression of AFP and cytokeratin 8 indicated that bone metastatic tumor cells were functional and retained their epithelial traits. These results are consistent with the previous in situ tumourigenesis assay. We conclude that LM3 and 97H cells have definite but limited potential to form bone metastasis, whilst 7721 cells are incapable of bone metastasis. Other sites of metastatic lesion formed include the lung, the subcutis, the liver, and the abdomen. As we mentioned before, tumor cell line is a heterogeneous mixture consisting of cell subpopulations with varying metastatic potential and different organ specificity. So, after the introduction of tumor cells into systematic circulation, it is conceivable that metastases may happen anywhere as long as there is arterial blood supply.

To acquire cells with a unique propensity for bone metastasis, we isolated four BM1 cell populations from metastases in hind limbs and mandible of LM3-inoculated mice. A series of in vitro assays were then performed to determine either any changes in phenotype had occurred to these BM1 cells after one cycle of in vivo selection, or did they remain a common progeny and share the same characteristics as their parental LM3 cells. Although all cell lines exhibited the same rate of proliferation, BM1 cells significantly outperformed LM3 cells in the soft agarose assay, the cell migration assay, and the collagen/Matrigel invasion assay. These results suggest that BM1 cells appeared to be more aggressive than their parental cells after one cycle of in vivo selection. More importantly, BM1 cells manifested an enhanced ability to form bone metastases as we expected, as well as a lower rate of non-bone metastasis when compared to LM3 cells. Combining these findings, we speculate that this specifically enhanced bone meta-static potential of BM1 cells is unrelated to their proliferation ability, but rather caused by acquisition of specific metastasis-promoting functions, including those aggressive behaviour and the ability to recruit osteoclasts, which will be discussed later. These specific metastasis-promoting functions may remould bone tissue, transforming it into an ideal environment that favours HCC metastasis. We are convinced that this specific bone metastatic ability, as well as other aggressive phenotypes, would be further magnified after another one or two additional cycles of in vivo selection.

How to Make the Goal Come True

In this study, we produced HCC bone metastasis in nude mice via intracardiac injection of HCC cell lines and demonstrated its satisfactory modelling of HCC bone metastasis in patients. From metastatic tumors in mouse bones, we isolated several cell populations with altered phenotype and enhanced ability to form bone metastases. We also examined the expression pattern of several metastasis-related genes in this model system, including those previously identified as breast cancer bone metastasis genes.

1. We established 97H and LM3 cell clones with stable expression of firefly luciferase (LUC).

2. We proved that HCC cells could form bone metastasis in nude mice via intratibial injection.

3. We reproduce HCC bone metastasis in nude mice via intracardiac injection of tumor cells.

4. We isolated the sub-population of tumor cells that targets metastasis to bone.

In procedure above, 97H and LM3 were highly metastatic HCC cell lines, which were stably transfected with luciferase gene.

In procedure above, BALB/cA-nu mice, 4-5 weeks old, were purchased from Beijing HFK Bioscience Co. Ltd. All the mice were maintained in laminar flow cabinets under SPF conditions and received human care throughout the entire study.

In procedure above, the whole procedure of animal experiments was in accordance with ARRIVE guidelines for animal experiments and was approbated by Hubei Provincial Laboratory Animal Association.

In procedure above, cell number for intratibial injection is $0.5\times10^6$. cell number for intracardiac injection is $1\times10^6$.

In procedure above, 27G syringes were used for intratibial injection. 29G syringes were used for intra-cardiac injection.

The models established in this manner bypass several early stages of metastasis, including cell detachment, EMT, and intravasation, but still provide a useful approximation to investigate the natural process of cancer metastasis in patients, especially in circulatory tumor cell homing and tumor-host/tumor-stroma interaction.

It is also recognized that the average tumor cell line is a heterogeneous mixture consisting of cell sub-populations with varying metastatic potential and different organ specificity during metastasis. By means of repetitive “heart to target site” in vivo selection, several cell sub-lines with organ-specific metastatic potential have been isolated from the above metastatic animal models and were found to harbor a distinct set of genes whose expression pattern favors such organ-specific metastasis.

To the best of our knowledge, the presented animal model of HCC bone metastasis is the first to be described, and it shares many similarities with HCC bone metastasis patients.

Based on SPECT scanning, HCC patients with bone metastases manifest increased radiotracer uptake in bones, typically characterising tumour-induced osteolysis accompanied by osteoblasis as compensation for bone loss. The clinical spectrum of HCC bone metastasis involves the vertebrae, the pelvis, the ribs/sternum, the skull, and the lower limbs, in a descending order. Our animal model has osteolytic lesions and similar SPECT features as well, and covers the full clinical spectrum, in spite of different incidence for individual bones.

DETAILED DESCRIPTION OF THE EMBODIMENTS

Figure 1A:
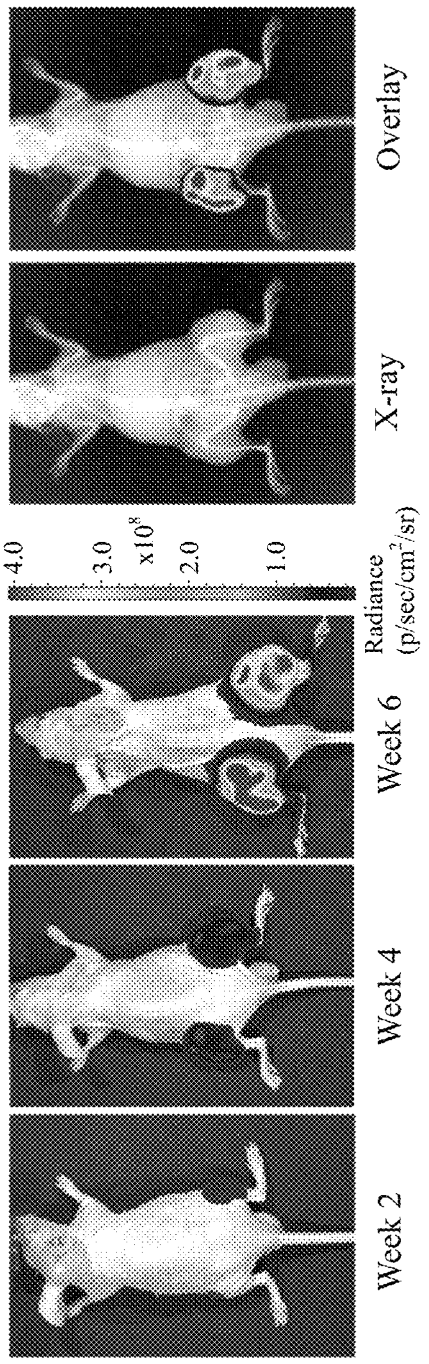
FIG. 1A illustrates luminescence signals of tumor cells detectable 14 days after intratibial injection and increased conspicuously on day 28 and day 42; the tumor-involved region roughly coincided with the contour of the knee and the tibia according to the merged image of X-ray and BLI; and a combined lesion of both osteolysis and osteoblasis along the tibia shaft was evident in the X-ray image.

To further illustrate the invention, experiments detailing a method for establishing an animal model of HCC bone metastasis are described below. It should be noted that the following examples are intended to describe and not to limit the invention.

Materials

Balb/c Nu/Nu Athymic Mice.

4-5 weeks old, All the mice were maintained in laminar flow cabinets under SPF conditions and received human care throughout the entire study. The whole procedure of animal experiments was in accordance with ARRIVE guidelines for animal experiments and was approbated by Hubei Provincial Laboratory Animal Association.

MHCC97H (97H) and HCCLM3 (LM3) cells engineered to express luciferase (97H/Luc+, LM3/Luc+).

97H and LM3 were purchased from Liver Cancer Institute of Zhongshan Hospital (Shanghai, China). All the cell lines had passed DNA fingerprinting, *mycoplasma* detection, isozyme detection, and cell vitality detection. These cell lines were expanded and cryopreserved immediately after receipt. Cross-contamination between different cell lines would not happen because all the cells we used in the experiments were resuscitated from that initial batch, and no more than six passages expanded in vitro. Both cell lines were transfected with PGL4.51 plasmid (Promega, WI, USA) using Lipofectamine LTX reagent (Invitrogen, California, USA). Cell clones with stable expression of firefly luciferase (LUC) were selected using 500 μg/ml G418 and subcultured in 10% FBS DMEM (Hyclone, Utah, USA) containing 200 μg/ml G418 for in vitro analysis and animal experiments.

Tissue Culture Facilities.

Sterile phosphate-buffered saline (PBS).

Selection of syringes and needles (29G).

Sterile surgical instruments.

Sutures.

Isoflurane gas anaesthesia system.

Caliper Lumina XR (Xenogen, MA, USA)

D-Luciferin, sodium salt (Gold-bio, USA).

Induction of Bone Metastases by Direct Intratibial Inoculation of Cancer Cells

Prepare a single cell suspension of 97H/Luc+ and LM3/Luc+ cells at a concentration of $0.5\times10^7$ cells/ml in ice-cold FBS-free DMEM medium.

Anaesthetize the mouse using isoflurane.

Fix the anaesthetized mouse in a supine position on a sterile surface.

Both hind limbs were prepared after sterilisation with 70% ethanol. The knee was held in a flexed position.

Aspirate the cell suspension into a 27G needle syringe, through a 100 μL pipette, avoiding air bubbles.

A 27G needle was used to penetrate the tibial plateau to reach the marrow cavity, where it was possible to inject fluid with little resistance.

Fifty microliters of 1:1 tumour cell/Matrigel (BD, NJ, USA) mixture was injected slowly.

Sterilize the limbs with 70% ethanol again, then put the mice back to the cages.

Monitor the development and progression of metastases twice a week by BLI.

Induction of Bone Metastases by Intra-Cardiac Injection of Cancer Cells

Harvest the 97H/Luc$^+$ and LM3/Luc$^+$ cells, pellet and wash several times in sterile PBS and suspended in ice-cold FBS-free DMEM medium at a density of $0.5\times10^7$/ml.

Prepare a suspension of 97H/Luc$^+$ and LM3/Luc$^+$ cells, by aspirating the cells up and down through a pipette. Equal volume of suspension was added in 29G syringes by pipette. Use a microscope to make sure that there are no clumps in the single cell suspension after 200 mesh cell screen (Solarbio., USA).

Anaesthetize the mice using isoflurane gas anaesthesia.

Fix the anaesthetized mouse in a supine position on a sterile surface with the head of the animal in a nozzle which supplies isoflurane at a maintenance dose of 2%.

Aspirate the cell suspension into a 29-G needle syringe, making sure that no air bubbles are present.

Carefully insert the needle through the diaphragm approximately 3 mm to the left of the sternum and aim centrally towards the heart.

Advance the needle into the left ventricle making sure that it is correctly positioned.

Slowly inject 100 μL of the cell suspension into the left ventricle over a period of 30 s.

Monitor the development and progression of metastases weekly by BLI.

Bioluminescence Imaging Using the IVIS Spectrum System

Throughout the entire procedure, mice should be observed for any signs of distress or changes in vitality.

1. Initialize the IVIS Spectrum imaging system.

2. Prepare a solution of sodium salt, D-luciferin at a concentration of 10 mg/ml in sterile PBS, and stock in −20° C.

3. Inject the animal intraperitoneally with 150 ml of the luciferin solution.

4. Allow the luciferin to distribute through the tissues in for over 5 mins.

5. Anaesthetize the mouse using isoflurane gas anaesthesia.

6. Select the field of view depending in the number of animals that will be imaged.

7. When fully anaesthetized, place the animal or animals in a supine position in the imaging chamber on the 37° C. movable imaging stage with constantly supplying isoflurane.

8. Start the image recording sequence.

9. Turn the mice from a ventral to a dorsal position and repeat the image recording.

10. Return the mice to their cages where they should recover consciousness quickly.

SPECT Bone Imaging

The existence of bone metastasis was also examined via SPECT scanning 4 weeks after intracardiac injection. For each mouse, approximately 0.2 μCi of Tc-99 m-MDP was injected through the tail vein. Bone scanning images were acquired 5 h after radiotracer injection using a SPECT/CT dual-modality imaging instrument with a total collected radiation of 100 kct.

Plane X-Ray Imaging

X-ray images were acquired concomitantly at final BLI scanning using the Caliper Lumina XR to detect the presence of visible osteolytic or osteoblastic lesions. Mice were anaesthetised, positioned supine, and exposed to 35 kV X-ray for 1.5 s.

Isolation and Subculturing of Bone Metastatic Cells

To isolate cells from bone metastatic tumours, mice were euthanised, and bones from BLI-suspected sites were resected from the body at the joints with the surrounding soft tissue removed. Excised bone was minced into tissue volumes of 1 $mm^3$ and incubated in RBC lysis buffer followed by collagenase/hyaluronidase (Sigma-Aldrich, MO, USA) digesting solution on a rocking plate. Cells were collected via centrifugation and seeded onto a 12-well plate. Culturing medium was replaced after 24 h to eliminate non-adherent cells. Cells were maintained in 10% FBS DMEM with 200 μg/ml G418.

Example 1 LM3 Cells Form Tumors In Situ after Intratibial Injection

Figure 1B:
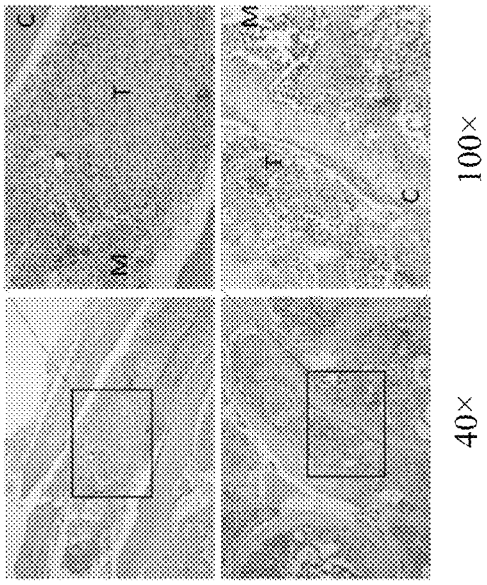
FIG. 1B illustrates histological sections revealed that tumor cells grew not only within the marrow cavity but also penetrated the bone cortex and invaded into the epiphysis and surrounding tissues.
Figure 1C:
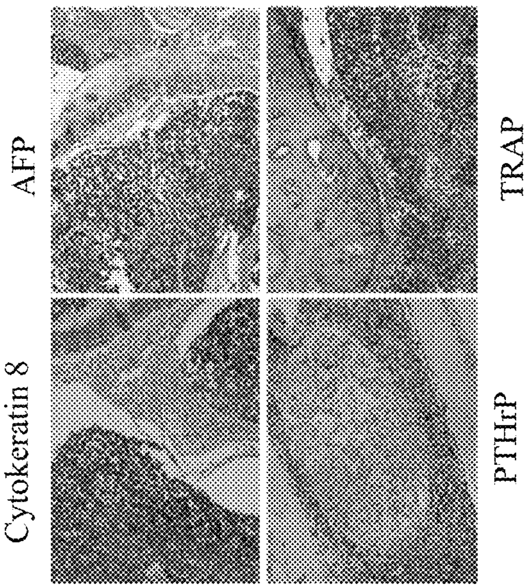
FIG. 1C illustrates that in situ-formed tumor cells were immunopositive for anti-AFP and anti-cytokeratin 8, but immunonegative for anti-PTHrP. The lytic tumor deposits did not contain osteoclasts, which appeared dark red in TRAP staining.

The luminescence signal of tumor cells was detectable 14 days after intratibial injection and increased conspicuously on day 28 and day 42 (FIG. 1A). The tumor-involved region roughly coincided with the contour of the knee and the tibia according to the merged image of X-ray and BLI. A combined lesion of both osteolysis and osteoblasis along the tibia shaft was evident in the X-ray image (FIG. 1A). Histological sections revealed that tumor cells grew not only within the marrow cavity but also penetrated the bone cortex and invaded into the epiphysis and surrounding tissues (FIG. 1B). In situ-formed tumor cells were immunopositive for anti-AFP and anti-cytokeratin 8, but immunonegative for anti-PTHrP. Notably, the lytic tumor deposits did not contain osteoclasts, which appeared dark red in TRAP staining (FIG. 1C). Both LM3 and 97H cells formed tumors in situ after intratibial injection.

A Post intratibial injection, mice were monitored by BLI and X-ray imagine every week. Combined lesion of osteolysis and osteoblasis was indicated by black arrow in the X-ray image.

B Histological sections of in situ tumours. T, C, and M denote tumor cells, cortical bone and normal bone marrow, respectively.

C Immunohistological sections of in situ tumors stained by indicated three antibodies and TRAP staining kit, respectively

Example 2 LM3 and BM1 Cells Metastasis to Bone after Intracardiac Injection

Figure 2A:
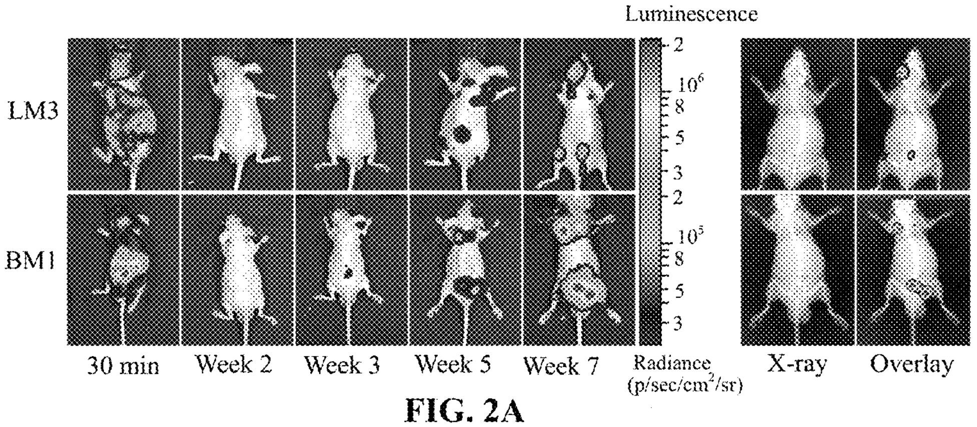
FIG. 2A are luminescence images showing that the formation of metastatic tumors was first detected on day 21 post-inoculation in most LM3- and 97H-injected mice, and tumors grow exponentially.
Figure 2B:
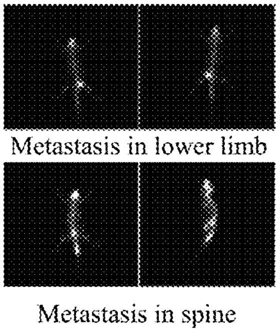
FIG. 2B illustrates bone lesions characterized by aggregated radiotracer when scanned via SPECT.
Figure 2C:
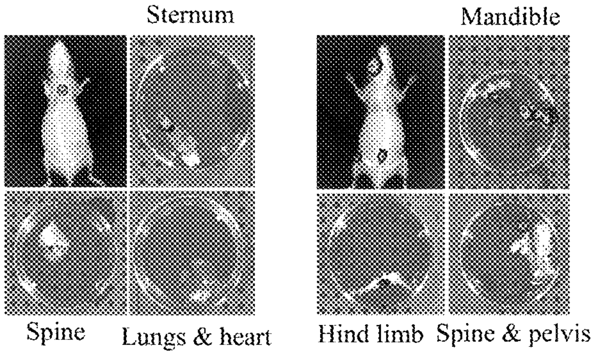
FIG. 2C illustrates post-mortem ex vivo BLI of suspected bone substantiated the uptake of disseminated tumor cells in bone but not in other surrounding tissues.
Figure 2D:
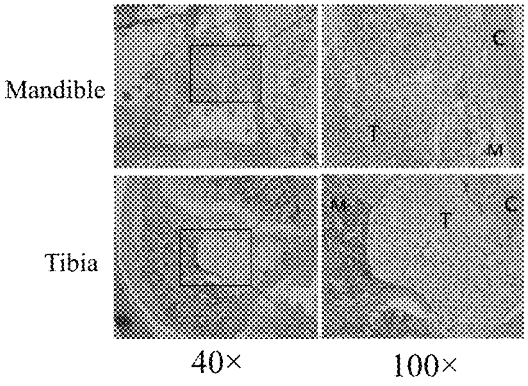
FIG. 2D illustrates histological sections clearly showed metastatic tumor cells in the tibia and the mandible, with destruction of normal bone tissue.
Figure 2E:
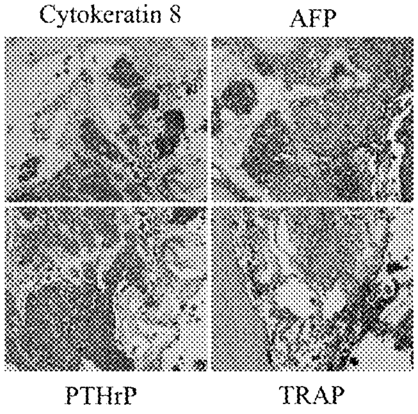
FIG. 2E illustrates immunostaining demonstrated that metastatic tumor cells expressed not only AFP and cytokeratin 8, but also PTHrP. TRAP staining revealed the presence of dark red-stained osteoclasts distributed within or around the tumor mass.

BLI was first performed immediately after cell inoculation. A successful intracardiac injection was identified by the distribution of luminescence signal throughout the whole body of the animal. The presence of signal confined within lungs or chest cavity indicated an unsuccessful injection, and these mice were excluded from further steps of this study. In most LM3- and 97H-injected mice, the formation of metastatic tumors was first detected on day 21 post-inoculation. The tumors grew exponentially as showed in serial images (FIG. 2A), causing bone lesions characterized by aggregated radiotracer when scanned via SPECT (FIG. 2B). The post-mortem ex vivo BLI of suspected bone substantiated the uptake of disseminated tumor cells in bone but not in other surrounding tissues (FIG. 2C). Histological sections clearly showed metastatic tumor cells in the tibia and the mandible, with destruction of normal bone tissue (FIG. 2D). Immunostaining demonstrated that metastatic tumor cells expressed not only AFP and cytokeratin 8, but also PTHrP. TRAP staining revealed the presence of dark red-stained osteoclasts distributed within or around the tumor mass (FIG. 2E).

A Serial BLI images and merged BLI/X-ray images of LM3 and BM1 injected mice in a unified color scale.

B SPECT bone scanning on day 30 of two representative mice with metastases in femur and spine, respectively. The site of bone metastasis was indicated by increased uptake of radiotracer.

C Ex vivo tissue BLI images of mice with bone metastasis. For the mouse shown on the left, the sternum, the spine, the heart, and the lung were excised and imaged. For the mouse shown on the right, the mandible, the pelvis, and the right hind limb were excised and imaged. The corresponding in vivo BLI images are also shown in the upper left.

D Histological sections of bone metastases in mandible and tibia. T, M, and C denote tumor cells, normal bone marrow, and cortical bone, respectively.

E Immunohistological sections of bone metastases stained by indicated three antibodies and TRAP staining kit, respectively. Dark red-stained osteoclasts were indicated by black arrow in TRAP staining section.

TABLE 1

| Distribution of metastatic tumors in mice inoculated with different HCC cell lines | | | | | | | | | |
|---|---|---|---|---|---|---|---|---|---|
| Cell line | Mouse | Skull | Spine | Fore limb | Femur | Knee/tibia | Pelvis | Ribs/sternum | Other |
| LM3 | 1 | | | | | | | | Lung |
| | 2 | + | | | + | | | + | Subcutis |
| | 3 | | | | | | | | |
| | 4 | + | + | | | + | | | |
| | 5 | | | | | | | | |
| | 6 | + | | | | | | | Abdomen |
| | 7 | | | | | | | | |
| | 8 | | + | | | | | + | |
| | 10 | | | | | | | | Lung |
| 97H | 11 | | | | | | | | Abdomen |
| | 12 | | | | | | | | |
| | 13 | + | | | | | | | |
| | 14 | | | | | | | | Lung |
| 7721 | 16 | | | | | | | | |
| | 17 | | | | | | | | |
| | 18 | | | | | | | | |
| | 19 | | | | | | | | |
| BM1-L1 | 31 | + | + | | | | | | |
| | 32 | + | + | | + | | | | Lung |
| | 33 | | | | | | | | |
| | 34 | + | | | + | | | | |
| | 35 | | | | | | | | |
| BM1-L2 | 21 | + | | | | + | | | |
| | 22 | + | + | | | | | | |
| | 23 | + | | | + | | | | |
| | 24 | | | | | | | | Abdomen |
| | 25 | | | | | | | + | |

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for establishing an animal model of hepatocellular carcinoma (HCC) bone metastasis, the method comprising:

1) transfecting 97H and LM3 cell clones with luciferase genes to yield 97H/Luc+ and LM3/Luc+ cells expressing firefly luciferase (LUC);

2) intracardially injecting the 97H/Luc+ and LM3/Luc+ cells into each nude mouse of a set of nude mice to induce the formation of metastatic 97H/Luc+ and LM3/Luc+ cells in bones of the set of nude mice, wherein the nude mice are 4-5-week-old BALB/cA-nu mice; and 3) isolating the metastatic 97H/Luc+ and LM3/Luc+ cells obtained in 2) from the bones of the set of nude mice.

2. The method of claim 1, wherein 2) comprises:

a) pelleting the 97H/Luc+ and LM3/Luc+ cells to yield a cell pellet comprising the 97H/Luc+ and LM3/Luc+ cells; and washing the cell pellet several times in sterile PBS;

b) suspending the cell pellet obtained in a) in an ice-cold FBS-free DMEM medium by pipetting the cell pellet up and down to yield a cell suspension having a concentration of $0.5\times10^7$ cells/ml; and filtering the cell suspension through a 200-mesh screen to yield a single cell suspension of the 97H/Luc+ and LM3/Luc+ cells, wherein the single cell suspension is a cell suspension comprising single cells of the 97H/Luc+ and LM3/Luc+ cells;

c) anaesthetizing each nude mouse of the set of nude mice using isoflurane gas anesthesia to obtain a set of anaesthetized nude mice;

d) fixing each nude mouse of the set of anaesthetized nude mice in a supine position on a sterile surface with the head of each nude mouse of the set of anaesthetized nude mice in a nozzle which supplies isoflurane at a maintenance dose of 2%;

e) aspirating the single cell suspension obtained in b) into a 29-G needle syringe for each nude mouse of the set of anaesthetized nude mice, and avoiding producing air bubbles in the 29-G needle syringe;

f) inserting the needle of the 29-G needle syringe through the diaphragm of each nude mouse of the set of anaesthetized nude mice approximately 3 mm to the left of the sternum of each nude mouse of the set of anaesthetized nude mice and positioning the needle of the 29-G needle syringe toward the heart of each nude mouse of the set of anaesthetized nude mice;

g) advancing the needle of the 29-G needle syringe into the left ventricle of each nude mouse of the set of anaesthetized nude mice;

h) injecting 100 μl of the single cell suspension into the left ventricle of each nude mouse of the set of anaesthetized nude mice over a period of 30 seconds by the 29-G needle syringe; and i) monitoring development and progression of the metastatic 97H/Luc+ and LM3/Luc+ cells weekly by monitoring LUC expression of the 97H/Luc+ and LM3/Luc+ cells in the bones of the set of nude mice using bioluminescence imaging (BLI).

3. The method of claim 1, wherein 3) comprises:

i) identifying bones comprising the metastatic 97H/Luc+ and LM3/Luc+ cells by identifying LUC expression of the 97H/Luc+ and LM3/Luc+ cells in bones of the set of nude mice using bioluminescence imaging (BLI);

ii) euthanizing the set of nude mice obtained in 2) to obtain euthanized nude mice;

iii) resecting the bones comprising the metastatic 97H/Luc+ and LM3/Luc+ cells from bodies of the euthanized nude mice and removing surrounding soft tissues of the bones to yield resected bones;

iv) mincing the resected bones to yield minced bones;

v) adding RBS lysis buffer and collagenase/hyaluronidase digesting solution to the minced bones to yield a mixture comprising the minced bones, the RBS lysis buffer, and the collagenase/hyaluronidase digesting solution;

vi) incubating the mixture obtained in v) on a rocking plate and then centrifuging the mixture to yield a metastatic cell pellet comprising the metastatic 97H/Luc+ and LM3/Luc+ cells;

vii) re-suspending the metastatic cell pellet obtained in vi) in 10% FBS DEME with 200 μg/ml G418 to yield a metastatic cell suspension;

viii) seeding the metastatic cell suspension onto a 12-well plate; and ix) renewing the 10% FBS DEME with 200 μg/ml G418 after 24 hours.

* * * * *